(12) United States Patent
Lu et al.

(10) Patent No.: US 10,674,962 B2
(45) Date of Patent: Jun. 9, 2020

(54) FINGER CLAMPING DEVICE AND OXIMETER USING THE SAME

(71) Applicant: Hangzhou Mega Inno of Health Technology Co. Ltd, Hangzhou (CN)

(72) Inventors: Zhan-Sheng Lu, Shenzhen (CN); Yu-Chun Sun, New Taipei (TW)

(73) Assignee: Hangzhou Jiangyu Innovation Medical Technology CO., LTD, Hangzhou (CN)

( * ) Notice: Subject to any disclaimer, the term of this patent is extended or adjusted under 35 U.S.C. 154(b) by 318 days.

(21) Appl. No.: 15/603,484

(22) Filed: May 24, 2017

(65) Prior Publication Data

US 2017/0340280 A1  Nov. 30, 2017

(30) Foreign Application Priority Data

May 24, 2016  (CN) .......................... 2016 1 0352317

(51) Int. Cl.
*A61B 5/00* (2006.01)
*A61B 5/1455* (2006.01)

(52) U.S. Cl.
CPC ........ *A61B 5/6838* (2013.01); *A61B 5/14551* (2013.01); *A61B 5/14552* (2013.01); *A61B 5/6826* (2013.01)

(58) Field of Classification Search
CPC .............. A61B 5/6838; A61B 5/14552; A61B 5/14551; A61B 5/6826
See application file for complete search history.

(56) References Cited

U.S. PATENT DOCUMENTS

| 6,654,621 | B2 * | 11/2003 | Palatnik ............. A61B 5/14552 600/322 |
| 7,239,905 | B2 * | 7/2007 | Kiani-Azarbayjany ..................... E02B 11/005 600/316 |
| 2010/0305417 | A1 * | 12/2010 | Kumazaki .......... A61B 5/14552 600/323 |

FOREIGN PATENT DOCUMENTS

JP  2007-289463 A  11/2007
JP  2010-273976 A  12/2010

\* cited by examiner

*Primary Examiner* — Eric F Winakur
*Assistant Examiner* — Abid A Mustansir
(74) *Attorney, Agent, or Firm* — ScienBiziP, P.C.

(57) ABSTRACT

A finger clamping device and an oximeter using the finger clamping device are provided. The finger clamping device includes a shell, an upper clamping member, and a lower clamping member. The shell includes two oppositely facing sidewalls. Each sidewall defines at least one sliding rail. The upper clamping member is arranged in the shell and defines two guiding rods. The two guiding rods are received in and slide along the sliding rail. At least one elastic member joins the lower clamping member and the upper clamping member and is tensioned when a finger is inserted between the upper clamping member and the lower clamping member.

8 Claims, 5 Drawing Sheets

FINGER CLAMPING DEVICE AND OXIMETER USING THE SAME

CROSS-REFERENCE TO RELATED APPLICATIONS

This application claims priority to Chinese Patent Application No. 201610352317.0 filed on May 24, 2016, the contents of which are incorporated by reference herein.

FIELD

The subject matter herein generally relates to medical apparatuses, and particularly to a finger clamping device and an oximeter using the same.

BACKGROUND

In medical field, an oximeter is used for measuring blood oxygen saturation of a human body and displaying pulses of a user. Generally, a finger clamping device needs to be manually pressed to clamp the finger of the user, which causes inconvenience.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Figure 1:
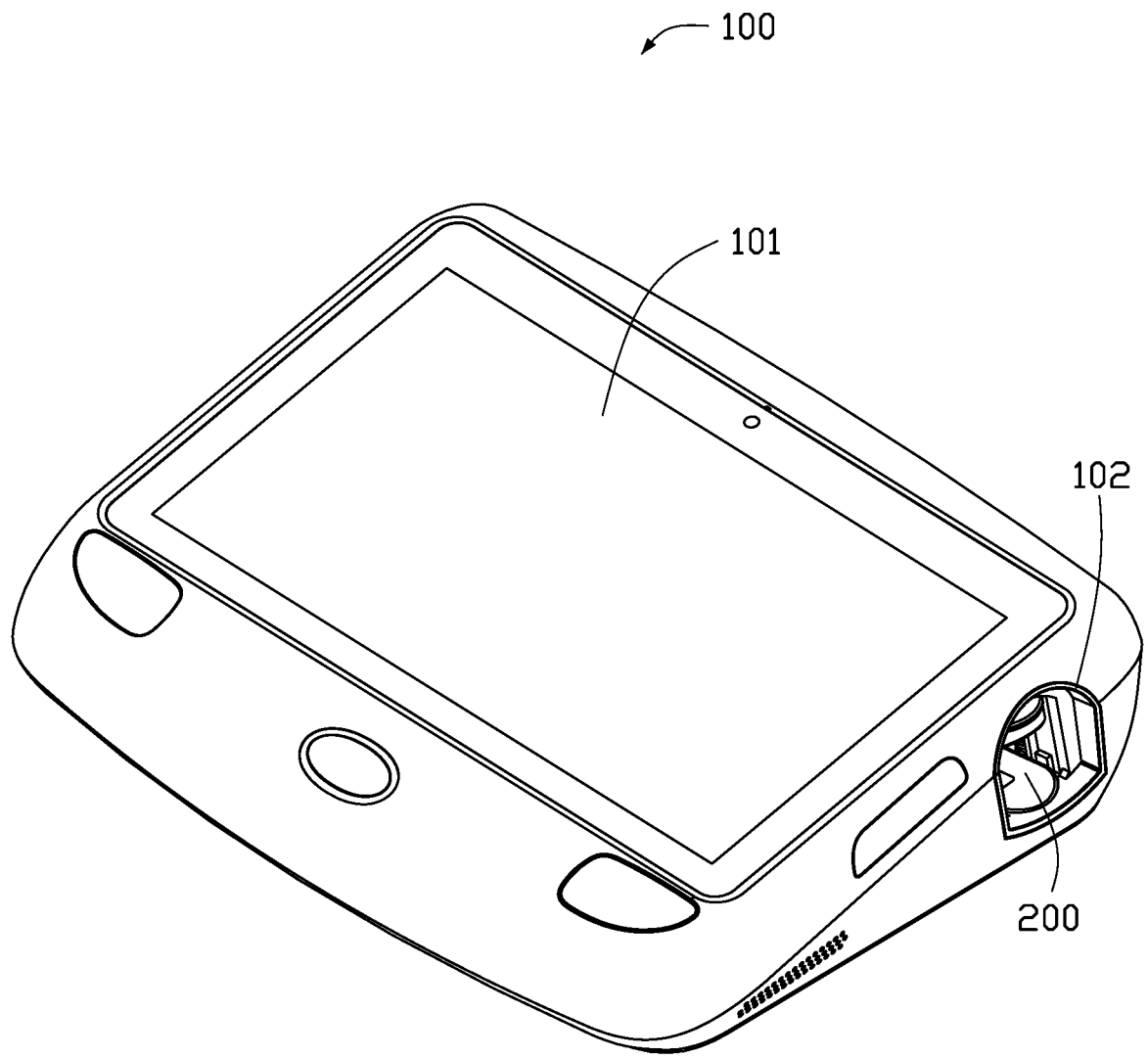
FIG. 1 is a schematic view illustrating an exemplary embodiment of an oximeter.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts have been exaggerated to better illustrate details and features of the present disclosure.

The present disclosure, including the accompanying drawings, is illustrated by way of examples and not by way of limitation. Several definitions that apply throughout this disclosure will now be presented. It should be noted that references to "an" or "one" exemplary embodiment in this disclosure are not necessarily to the same exemplary embodiment, and such references mean "at least one".

The term "comprising" means "including, but not necessarily limited to", it specifically indicates open-ended inclusion or membership in a so-described combination, group, series, and the like.

FIG. 1 illustrates an exemplary embodiment of an oximeter 100. In at least one exemplary embodiment, the oximeter 100 includes a main body 101 and a finger clamping device 200. The main body 101 defines an opening 102. The finger clamping device 200 is arranged in the opening 102. The finger clamping device 200 is used for clamping at least one finger of a user to measure blood oxygen saturation of the user. FIG. 1 illustrates only one example of the oximeter 100, other examples can include more components than as illustrated.

Referring to FIGS. 2-5, the finger clamping device 200 includes a shell 10, an upper clamping member 20, a lower clamping member 30, at least one elastic member 40, and a measuring device 50.

Figure 3:
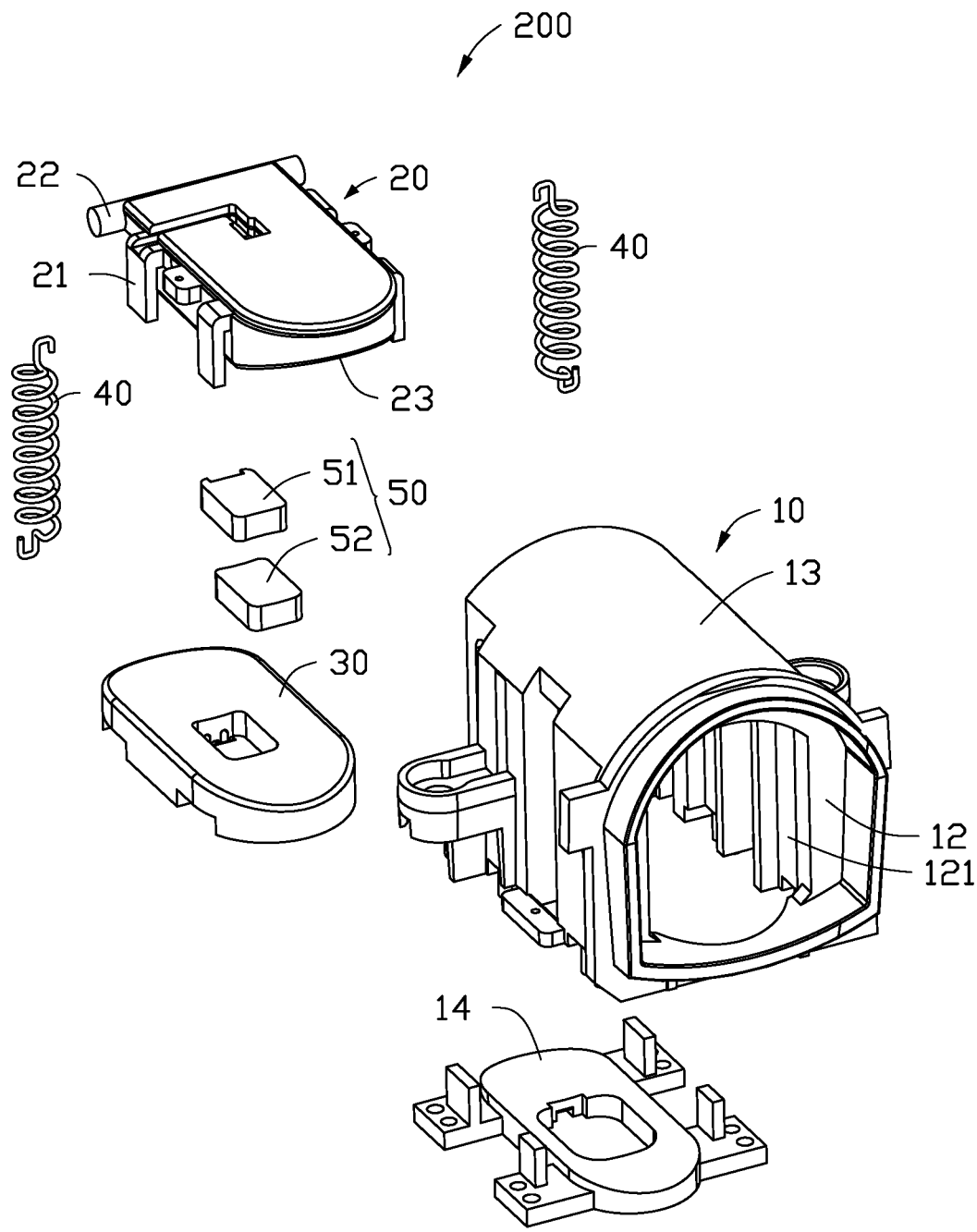
FIG. 3 is an exploded view illustrating an exemplary embodiment of a finger clamping device.
Figure 4:
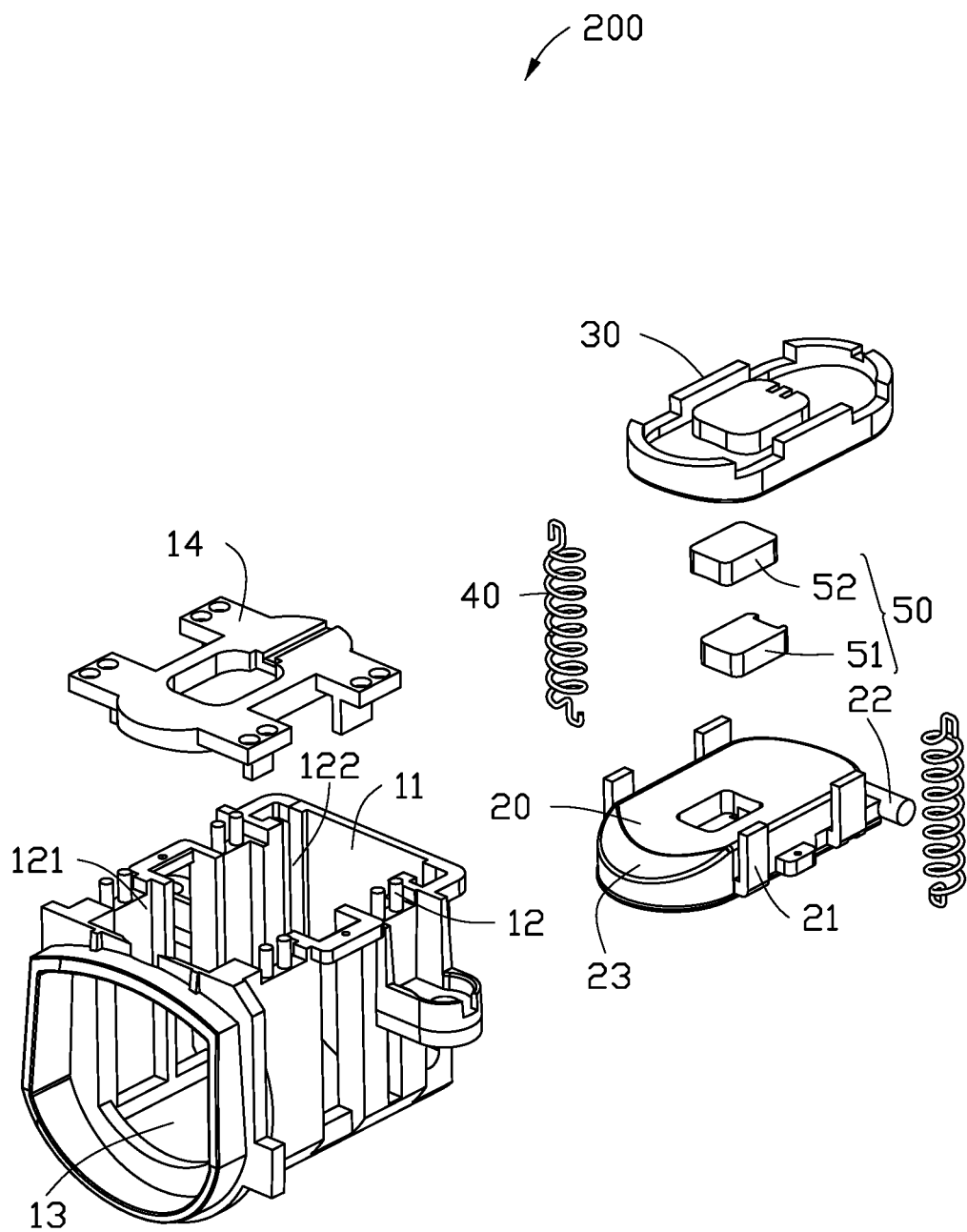
FIG. 4 is an exploded view from another angle of the finger clamping device in FIG. 3.
Figure 5:
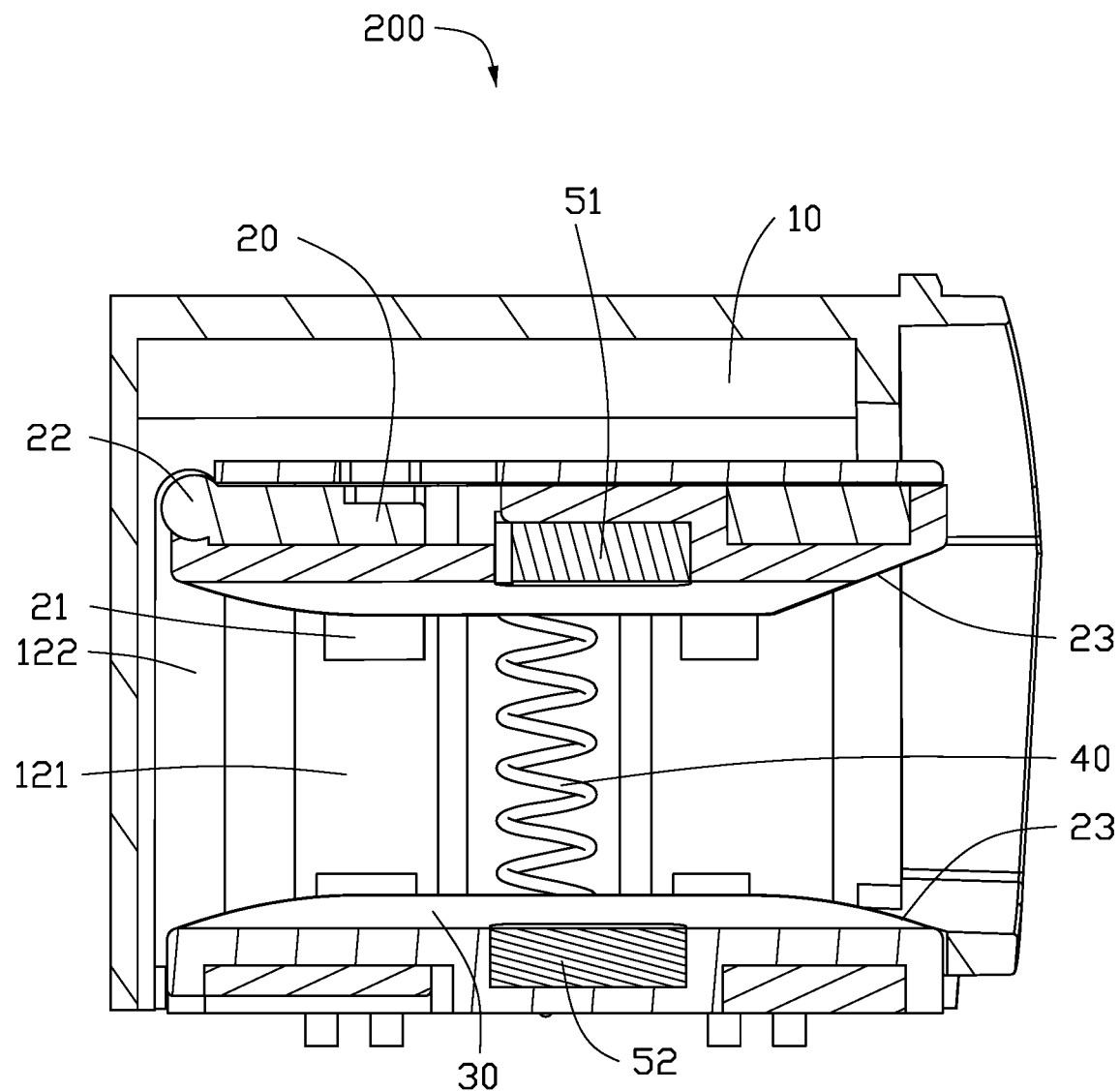
FIG. 5 is a cross-section view illustrating an exemplary embodiment of the finger clamping device.

A shape of the shell 10 matches with a shape of the opening 102. The shell 10 is received in the opening 102. In at least one exemplary embodiment, the shell 10 includes an inner wall 11, two sidewalls 12, a top surface 13, and a bottom surface 14 as shown in FIG. 3. The two sidewalls 12 are oppositely facing, each sidewall 12 defines at least one sliding rail 121. The at least one sliding rail 121 is extended along the sidewall 12 from the top surface 13 to the bottom surface 14. In at least one exemplary embodiment, each of the sidewalls 12 defines two sliding rails 121 which are parallel with each other. In other exemplary embodiments, a quantity of the sliding rails 121 can be other value. Each of the two sidewalls 12 further defines a sliding groove 122 as shown in FIG. 3, which is arranged close to the inner wall 11. The sidewall 12 has portions defining the sliding groove 122, the portions defining the sliding groove 122 has a strip shape and are parallel with the sliding rail 121.

The upper clamping member 20 and the lower clamping member 30 are arranged in the shell 10. In at least one exemplary embodiment, the upper clamping member 20 and the lower clamping member 30 are elongated members, and match with a shape of a human finger, accordingly, the finger clamping device 200 provides more comfort when clamping the finger of the user.

Two opposite sides of the upper clamping member 20 each define at least one guiding rod 21. Each guiding rod 21 is received in one of the sliding rails 121 on the sidewall 12, and can slide along the sliding rail 121. The lower clamping member 30 is mounted on the bottom surface 14. The upper clamping member 20 is connected in parallel to the lower clamping member 30 through the elastic member 40. In at least one exemplary embodiment, when the upper clamping member 20 and the lower clamping member 30 is in contact with each other, the upper clamping member 20 and the lower clamping member 30 is in a natural state.

In at least one exemplary embodiment, the finger clamping device 200 includes two elastic members 40, the two elastic members 40 are respectively coupled to two guiding rods 21 at the two sides of the upper clamping member 20. One end of each elastic member 40 is connected to the upper clamping member 20, the other end is connected to the lower clamping member 30, thereby the upper clamping member 20 is connected in parallel to the lower clamping member 30 through the elastic member 40. The upper clamping member 20 further includes a spindle 22. Two ends of the spindle 22 are respectively received in the sliding grooves 122 of the two sidewalls 12, and can slide along the sliding grooves 122. Thus, the spindle 22 is arranged at one end of the upper clamping member 20 towards the inner wall 11.

Figure 2:
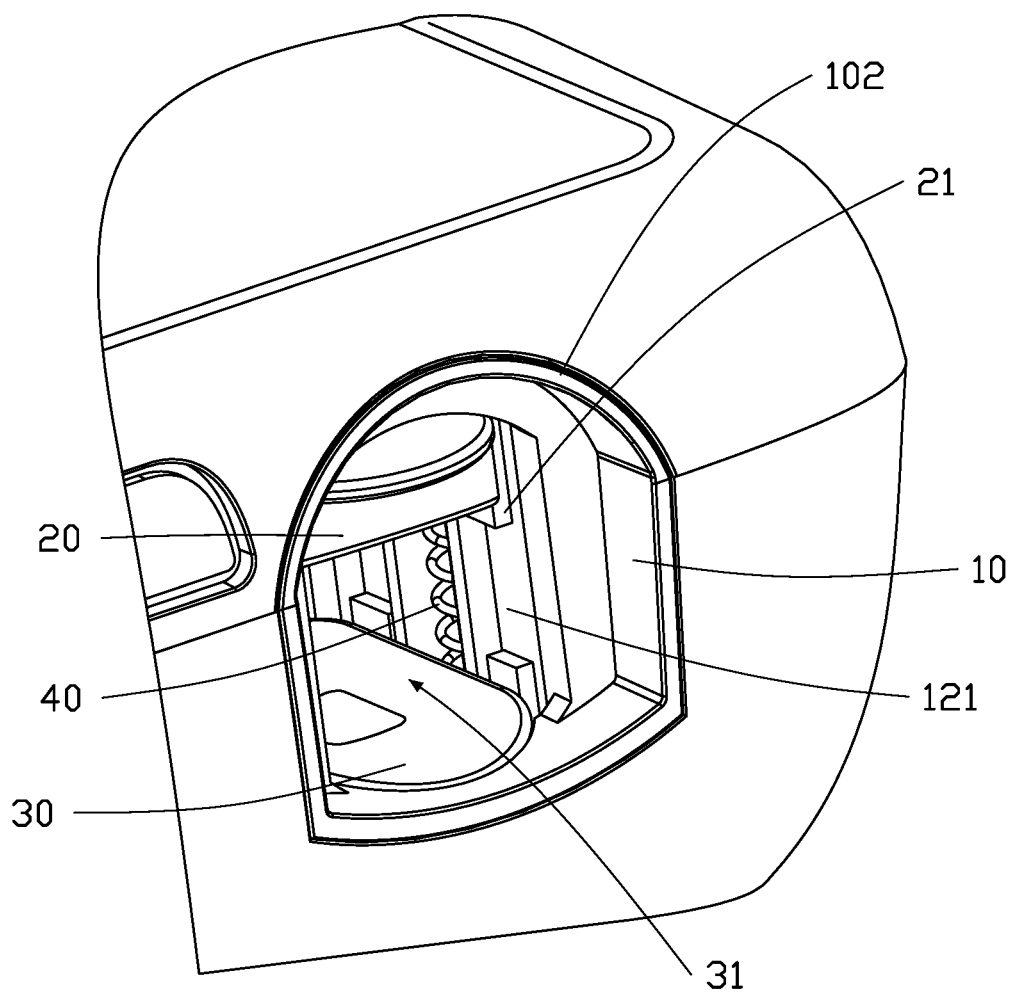
FIG. 2 is an enlarged view of a portion of the oximeter of FIG. 1.

In at least one exemplary embodiment, the upper clamping member 20 and the lower clamping member 30 each define an inclined surface 23. The inclined surface 23 of the upper clamping member 20 and the inclined surface 23 of the lower clamping member 30 are arranged away from the inner wall 11 and are oppositely facing, thus, an opening 31, as shown in FIG. 2, is formed between the upper clamping member 20 and the lower clamping member 30. In at least one exemplary embodiment, the opening 31 is trumpet-shaped, thus, the opening 31 enables the finger of the user to be conveniently and comfortably inserted into the finger clamping device 200.

In at least one exemplary embodiment, the upper clamping member 20 and lower clamping member 30 can be made from plastic or rubber material.

In other exemplary embodiments, the lower clamping device 30 can have a structure substantially the same as that of the upper clamping member 20, that is, the upper clamping member 20 and the lower clamping device 30 can both slide along the sliding rail 121.

The measuring device 50 is arranged in the finger clamping device 200. The measuring device 50 is used for measuring the blood oxygen saturation of the user. In at least one exemplary embodiment, the measuring device 50 includes an infrared transmitter 51 and an infrared receiver 52. The infrared transmitter 51 is arranged on either the upper clamping member 20 or the lower clamping member 30. The infrared receiver 52 is arranged on either the upper clamping member 20 or the lower clamping member 30. For example, the upper clamping member 20 may carry the infrared transmitter 51, and the lower clamping device 30 may carry the infrared receiver 52 or vice versa.

When the finger of the user is clamped between the upper clamping member 20 and the lower clamping device 30, the infrared transmitter 51 transmits infrared rays, the infrared receiver 52 receives the infrared rays after the infrared rays go through the clamped finger. The processor (not shown) of the oximeter 100 measures the blood oxygen saturation according to the infrared rays received by the infrared receiver 52.

When the finger of the user is inserted into the opening 31 between the upper clamping member 20 and the lower clamping member 30, the end having the inclined surface 23 of the upper clamping member 20 is driven to move away from the lower clamping member 30 by the finger. At this time, the upper clamping member 20 rotates about the spindle 22. When the upper clamping member 20 keeps on moving away from the lower clamping member 30, the spindle 22 moves towards the top surface 13 along the sliding groove 122, the guiding rod 21 moves towards the top surface 13 along the sliding rail 121. At this time, the elastic members 40 are stretched, the finger is tightly clamped by the upper clamping member 20 and the lower clamping member 30 with an elastic restoring force of the stretched elastic members, thereby the oximeter 100 can conveniently measure the blood oxygen saturation of the user.

When the finger of the user is clamped by the upper clamping member 20 and the lower clamping member 30, external light is blocked out by the shell 11, and cannot reach the measuring device 50, thereby measurements are more accurate. When the finger of the user is withdrawn from the opening 31 between the upper clamping member 20 and the lower clamping member 30, the upper clamping member 20 is driven to return to an initial position by the elastic restoring force of the elastic member 40.

It is believed that the present embodiments and their advantages will be understood from the foregoing description, and it will be apparent that various changes may be made thereto without departing from the spirit and scope of the disclosure or sacrificing all of its material advantages, the examples hereinbefore described merely being exemplary embodiments of the present disclosure.

What is claimed is:

1. A finger clamping device comprising:
a shell comprising two oppositely facing sidewalls, each sidewall defining at least one sliding rail;
an upper clamping member arranged in the shell, wherein two sides of the upper clamping member each define at least one guiding rod, each guiding rod is received in the sliding rail and slides along the sliding rail, each of the two sidewalls further defines a sliding groove, the upper clamping member further defines a spindle, the spindle is received in the sliding grooves;
at least one elastic member; and
a lower clamping member coupled to the upper clamping member through the at least one elastic member;
wherein when a finger is inserted between the upper clamping member and the lower clamping member, the upper clamping member is driven to rotate about the spindle, and the spindle is driven to slide along the sliding groove, then the elastic member is stretched, the finger is clamped by the upper clamping member and the lower clamping member with an elastic restoring force.

2. The finger clamping device according to claim 1, wherein two opposite sides of the upper clamping member and the lower clamping member each define an inclined surface, thereby an opening is formed between the upper clamping member and the lower clamping member, the opening is used for inserting the finger.

3. The finger clamping device according to claim 1, wherein the upper clamping member and the lower clamping member are made from plastic or rubber material.

4. The finger clamping device according to claim 1, further comprising a measuring device, wherein the measuring device comprises an infrared transmitter and an infrared receiver, when the infrared transmitter is arranged on the upper clamping member, the infrared receiver is arranged on the lower clamping member, when the infrared transmitter is arranged on the lower clamping member, the infrared receiver is arranged on the upper clamping member.

5. An oximeter comprising:
a main body defining an opening; and
a finger clamping device arranged in the opening, the finger clamping device comprising:
a shell comprising two oppositely facing sidewalls, each sidewall defining at least one sliding rail;
an upper clamping member arranged in the shell, wherein two sides of the upper clamping member each define at least one guiding rod, each guiding rod is received in the sliding rail and slides along the sliding rail, each of the two sidewalls further defines a sliding groove, the upper clamping member further defines a spindle, the spindle is received in the sliding grooves;
at least one elastic member; and
a lower clamping member coupled to the upper clamping member through the at least one elastic member;
wherein when a finger of is inserted between the upper clamping member and the lower clamping member, the upper clamping member is driven to rotate about the spindle, and the spindle is driven to slide along the sliding groove, then the elastic member is stretched, the finger is clamped by the upper clamping member and the lower clamping member with an elastic restoring force.

6. The oximeter according to claim 5, wherein two opposite sides of the upper clamping member and the lower clamping member define each an inclined surface, thereby an opening is formed between the upper clamping member and the lower clamping member, the opening is used for inserting the finger.

7. The oximeter according to claim 5, wherein the upper clamping member and the lower clamping member are made from plastic or rubber material.

8. The oximeter according to claim 5, further comprising a measuring device, wherein the measuring device comprises an infrared transmitter and an infrared receiver, when the infrared transmitter is arranged on the upper clamping member, the infrared receiver is arranged on the lower clamping member, when the infrared transmitter is arranged on the lower clamping member, the infrared receiver is arranged on the upper clamping member.

* * * * *